United States Patent [19]

Goto

[11] Patent Number: 4,908,152
[45] Date of Patent: Mar. 13, 1990

[54] CYCLOHEXANE DERIVATIVE

[75] Inventor: Yasuyuki Goto, Chibaken, Japan

[73] Assignee: Chisso Corporation, Osaka, Japan

[21] Appl. No.: 331,379

[22] Filed: Mar. 31, 1989

[30] Foreign Application Priority Data

Apr. 21, 1988 [JP] Japan ................................. 63-99180

[51] Int. Cl.⁴ ......................... G02F 1/13; C09K 19/30; C07C 25/13
[52] U.S. Cl. ............................ 252/299.63; 252/299.5; 350/350 R; 350/350 S; 570/129; 570/182
[58] Field of Search ........................ 252/299.63, 299.5; 350/350 R, 350 S; 570/129, 182

[56] References Cited

U.S. PATENT DOCUMENTS

| | | | |
|---|---|---|---|
| 4,368,135 | 1/1983 | Osman | 252/299.63 |
| 4,405,488 | 9/1983 | Sugimori et al. | 252/299.63 |
| 4,415,470 | 11/1983 | Eidenschink et al. | 252/299.63 |
| 4,422,951 | 12/1983 | Sugimori et al. | 252/299.63 |
| 4,490,305 | 12/1984 | Eidenschink et al. | 252/299.63 |
| 4,536,321 | 8/1985 | Sugimori et al. | 252/299.63 |
| 4,548,731 | 10/1985 | Sugimori et al. | 252/299.63 |
| 4,551,264 | 11/1985 | Eidenschink et al. | 252/299.63 |
| 4,620,938 | 11/1986 | Romer et al. | 252/299.63 |
| 4,808,333 | 2/1989 | Huynh-ba et al. | 252/299.63 |

FOREIGN PATENT DOCUMENTS 59-16840  1/1984  Japan .............................. 252/299.63

Primary Examiner—Teddy S. Gron
Attorney, Agent, or Firm—Wenderoth, Lind & Ponack

[57] ABSTRACT

A novel liquid crystal compound useful as a component of liquid crystal compositions, and particularly suitable to improvement in low temperature characteristics, and a liquid crystal composition containing the compound are provided, which compound is a 2-alkyl-5-[trans-4-(trans-4-alkylcyclohexyl)cyclohexyl]fluorobenzene expressed by the formula

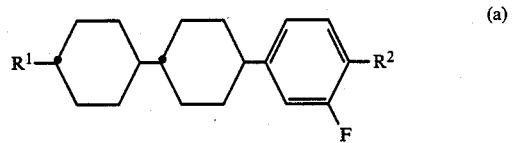

(a)

wherein $R^1$ and $R^2$ each represent an alkyl group of 2 to 10 carbon atoms.

8 Claims, No Drawings

CYCLOHEXANE DERIVATIVE

BACKGROUND OF THE INVENTION

1. Field of the Invention

This invention relates to a novel liquid crystal substance exhibiting liquid crystal phases within a broad temperature range, a good stability and a low viscosity.

2. Description of the Related Art

Liquid crystal display elements utilize the optical anisotropy and dielectric anisotropy of liquid crystal substances, and are classified into those of various modes such as TN mode (Twisted Nematic mode), DS mode (Dynamic Scattering mode), guest-host mode, DAP mode, etc. depending upon their display modes, but their properties suitable to the respective uses thereof are different. It is, however, common to any of liquid crystal substances that they must to be stable to moisture, air, heat, light, etc., and further, they should exhibit liquid crystal phases within a temperature range as broad as possible, and also should have optimum dielectric anisotropy values varied depending upon the kinds of display elements.

At present, however, there is no single compound satisfying all of such requirements, but it is the present status that liquid crystal compositions obtained by blending several kinds of liquid crystal compounds or non-liquid crystal compounds have been used. Recently, display elements operated over a range from low temperatures (about −40° C.) to high temperatures (about 80°–90° C.) have come to be particularly required; thus liquid crystal compositions having superior operating characteristics within a broader temperature range have been desired.

SUMMARY OF THE INVENTION

The object of the present invention is to provide a novel liquid crystal compound useful as a component of such liquid crystal compositions and particularly suitable to improvement in low temperature characteristics.

The present invention resides in 2-alkyl-5-[trans-4-(trans-4-alkylcyclohexyl)cyclohexyl]fluorobenzenes expressed by the formula

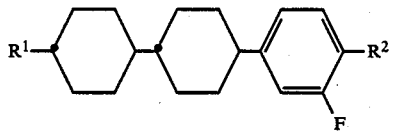

(a)

wherein $R^1$ and $R^2$ each represent an alkyl group of 2 to 10 carbon atoms, and a liquid crystal composition containing the same.

DETAILED DESCRIPTION OF PREFERRED EMBODIMENTS

The above $R^1$ and $R^2$ in the formula (I) each are preferred to be an alkyl group of 2 or 3 carbon atoms.

The compound of the present invention exhibits a small positive dielectric anisotropy value, a broad mesomorphic range, a particularly high liquid crystal-clearing point (N-I point) and yet a low viscosity and also a good stability to heat, air, moisture, light, etc.; hence the compound is very useful for obtaining liquid crystal compositions operated over a range from low temperatures to high temperatures.

Further, the compound of the present invention has a far superior compatibility with other liquid crystal compounds such as biphenyls, esters, Schiff's bases, phenylcyclohexanes, heterocyclic liquid crystals, etc. at low temperatures and also a broad mesomorphic range; hence when the compound of the present invention is blended with another nematic liquid crystal compound, it is possible to obtain a liquid crystal composition having broad liquid crystal phases over a range from low temperatures to high temperatures and also a low viscosity.

In addition, Japanese patent publication No. Sho 62-39136/1987 discloses compounds of the following formula similar to the compound of the present invention:

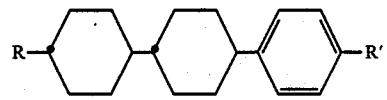

wherein R represents an alkyl group of 1 to 10 carbon atoms and R' represents an alkyl group or an alkoxy group each of 1 to 10 carbon atoms.

However, the above compound is somewhat unsatisfactory in compatibility at low temperatures, whereas the compound of the present invention has sufficiently improved compatibility at low temperatures.

Next, a process for producing the compound of the present invention will be illustrated.

3-Fluoro-bromobenzene (I) is reacted with metallic magnesium to obtain 3-fluorophenylmagnesium bromide (II), followed by reacting this compound with a 4-(trans-4-alkylcyclohexyl) cyclohexanone (III) (obtained by oxidizing the corresponding cyclohexanol) to obtain a 3-[1-hydroxy-4-(trans-4-alkylcyclohexyl)cyclohexyl]-fluorobenzene (IV), subjecting this compound to dehydration reaction using a suitable acid catalyst to obtain a 3-[4-(trans-4-alkylcyclohexyl)cyclohexen-1-yl]fluorobenzene (V), subjecting this compound to catalytic reduction reaction using a Raney nickel catalyst in an organic solvent such as ethyl alcohol at normal pressures and normal temperatures (25° C.) to obtain a 3-[4-(trans-4-alkylcyclohexyl)cyclohexyl]-fluorobenzene which is a mixture of stereoisomers of trans-form and cis-form, recrystallizing this compound from a suitable solvent to obtain a 3-[trans-4-alkylcyclohexyl)cyclohexyl]fluorobenzene (VI), reacting this compound with anhydrous aluminum chloride and a fatty acid chloride in nitrobenzene solvent to obtain a 2-alkanoyl-5-[trans-4-(trans-4-alkylcyclohexyl) cyclohexyl]fluorobenzene (VII) and successively subjecting this compound to a purification treatment according to a suitable reduction method to obtain the objective 2-alkyl-5-[trans-4-(trans-4-alkylocyclohexyl) cyclohexyl]fluorobenzene (a).

The foregoing will be illustrated by the following equations;

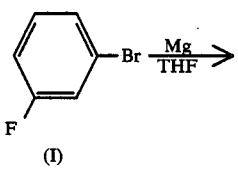

(I)

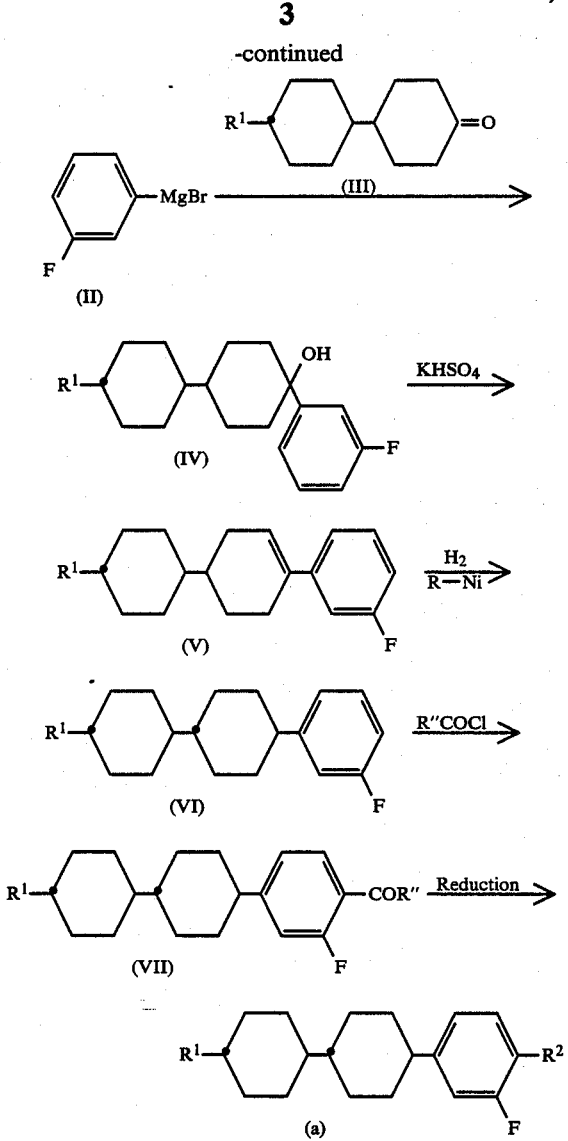

The above R" represents an alkyl group of 1 to 9 C.

Next, a process for producing the compound of the present invention and its use will be described in more detail.

EXAMPLE 1

Preparation of 2-ethyl-5-[trans-4-(trans-4-propylcyclohexyl) cyclohexyl]fluorobenzene (a compound of the formula (a) wherein $R^1=C_3H_7$ and $R^2=C_2H_5$)

(i) Slaked magnesium (4.8 g, 0.2 mol) was placed in a three-necked flask, followed by slowly dropwise adding a solution of 3-fluorobromobenzene (I) (35.0 g, 0.2 mol) dissolved in anhydrous tetrahydrofuran (50 ml) in nitrogen gas current with stirring while keeping the reaction temperature at 30°–35° C. to obtain a black-gray colored, uniform tetrahydrofuran solution of 3-fluorophenylmagnesium bromide (II), dropwise adding to this solution, a solution of 4-(trans-4-propylcyclohexyl)cyclohexanone (a compound of the formula (III) wherein $R^1=C_3H_7$) (46.7 g, 0.21 mol) dissolved in tetrahydrofuran (50 ml) over 30 minutes while keeping the reaction temperature at 5°–10° C., raising the temperature up to 35° C. after completion of the dropwise addition, aging the resulting solution for one hour, adding 3N hydrochloric acid (100 ml), extracting the resulting separated oily substance with toluene (100 ml) with stirring, washing the extract solution with water until the washing water became neutral to obtain a toluene solution of a 3-[1-hydroxy-4-(trans-4-propylcyclohexyl)cyclohexyl]-fluorobenzene (a compound of the formula (IV) wherein $R^1=C_3H_7$), adding potassium hydrogen sulfate (3.2 g) to the toluene extract solution, removing the resulting water in the form of an azeotrope with toluene under reflux on heating, washing the toluene solution after completion of the reaction with water until the washing water became neutral, distilling off toluene to obtain a concentrated substance of 3-[4-(trans-4-propylcyclohexyl)cyclohexen -1-yl]fluorobenzene (a compound of the formula (V) wherein $R^1=C_3H_7$), dissolving this substance without purification in ethyl alcohol (200 ml), subjecting the solution to catalytic reduction reaction using a developed Raney Ni (2.0 g) as a catalyst under the atmospheric pressure and at 25° C., filtering off Raney Ni after hydrogen absorption has ceased, distilling off ethyl alcohol from the ethyl alcohol filtrate and recrystallizing the residue from ethyl acetate, to obtain 3-[trans-4-(trans-4-propylcyclohexyl)-cyclohexyl]fluorobenzene (a compound of the formula (VI) wherein $R^1=C_3H_7$) . (38.7 g).

(ii) Successively, anhydrous aluminum chloride (30.8 g, 0.23 mol) was dissolved in nitrobenzene (150 ml), followed by adding to the solution, the total quantity of the above compound 3-[trans-4-(trans-4-propylcyclohexyl)cyclohexyl]fluorobenzene (38.7 g) at room temperature, dissolving the mixture together with stirring, adding acetyl chloride (27.3 g, 0.348 mol) over 15 minutes, reacting the mixture on heating at a reaction temperature of 35°–40° C. for 2 hours, adding the reaction solution after completion of the reaction to a mixture of 6N hydrochloric acid (50 ml) with ice water (500 g) to subject them to decomposition reaction, adding toluene (500 ml) to extract the resulting oily layer, washing the extract solution with an aqueous solution of sodium hydrogen carbonate, further washing it with water until the washing water became neutral, distilling off toluene and nitrobenzene and recrystallizing the residue from ethyl acetate to obtain 2-acetyl-5-[trans-4-(trans-4-propylcyclohexyl)cyclohexyl]fluorobenzene (a compound of the formula (VII) wherein $R^1=C_3H_7$ and $R''=CH_3$) (23.8 g). This product exhibited liquid crystal phases and had a crystal-nematic phase transition point (C-N point) of 90.5° C. and a nematic phase-isotropic liquid phase transition point (N-I point) of 204.7° C. (iii) Successively, the compound 2-acetyl-5-[trans-4-(trans-4-propylcyclohexyl) cyclohexyl]fluorobenzene (23.8 g) was added to diethylene glycol (100 ml), followed by agitating the mixture, adding hydrazine hydrate (17.9 g) and potassium hydroxide (20.1 g), gradually raising the temperature with stirring to react the mixture at 180° C. for 3 hours, allowing the resulting material to cool down to room temperature, adding water (500 ml), extracting the deposited crystals with toluene (100 ml), washing the extract solution with water, drying it over anhydrous sodium sulfate, distilling off toluene and recrystallizing from ethyl acetate to obtain 2-ethyl-5-[trans-4-(trans-4-propylcyclohexyl)cyclohexyl]fluorobenzene (15.2 g).

This product exhibited liquid crystal phases and had a crystal-smectic phase transition point (C-S point) of 40.6° C., a smectic phase-nematic phase transition point (S-N point) of 101.8° C. and a nematic phase-isotropic liquid phase transition point (N-I point) of 129.3° C.

EXAMPLES 2 AND 3

The following compounds were prepared in the same manner as in Example 1:

2-ethyl-5-[trans-4-(trans-4-ethylcyclohexyl)cyclohexyl]fluorobenzene
C-S point: 47.2° C.,
S-I point: 103.3° C.

2-propyl-5-[trans-4-(trans-4-propylcyclohexyl)cyclohexyl]fluorobenzene
C-S point: 20.6° C.
S-N point: 134.6° C.
N-I point: 146.9° C.

EXAMPLE 4

(composition)

A liquid crystal composition (A) consisting of
trans-4-propyl-(4-cyanophenyl)cyclohexane: 30% by weight
trans-4-pentyl-(4-cyanophenyl)cyclohexane: 40% by weight and
trans-4-heptyl-(4-cyanophenyl)cyclohexane: 30% by weight,
had a N-I point of 52° C. and a viscosity at 20° C. of 22.5 cp.

When 2-ethyl-5-[trans-4(trans-4-propylcyclohexyl)-clohexyl]fluorobenzene (15% by weight) as a compound of the present invention obtained in Example 1 was added to the above liquid crystal composition (A) (85% by weight), the N-I point of the resulting liquid crystal composition rose up to 58.2° C. and its viscosity at 20° C. somewhat rose up to 24.3 cp. Even when this liquid crystal composition was allowed to stand in a freezer at −40° C. for one month, no crystal deposited.

In addition, for comparison, a liquid crystal composition consisting of the above liquid crystal composition (A) (85% by weight) and 4-ethyl-[trans-4-(trans-4-propylcyclohexyl) cyclohexyl]benzene as one of the compounds of the above-mentioned formula disclosed in Japanese patent publication No. Sho 62-39136 (15% by weight) was prepared and allowed to stand in a freezer at −40° C. As a result, crystal deposition began to occur in three days.

What I claim is:

1. A liquid crystal compound having a low-temperature compatibility with other liquid crystal compounds, which compound is a 2-alkyl-5-[trans-4-(trans-4-alkylcyclohexyl) cyclohexyl]fluorobenzene expressed by the formula

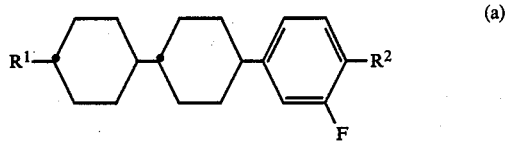

(a)

wherein $R^1$ represents an alkyl group of 2 to 10 carbon atoms and $R^2$ represents an alkyl group of 2 to 10 carbon atoms.

2. A liquid crystal compound according to claim 1, wherein said $R^1$ and $R^2$ each represent an alkyl group of 2 or 3 carbon atoms.

3. A liquid crystal compound according to claim 1, which is 2-ethyl-5-[trans-4-(trans-4-propylcyclohexyl)-cyclohexyl]fluorobenzene.

4. A liquid crystal compound according to claim 1, which is 2-ethyl-5-[trans-4-(trans-4-ethylcyclohexyl)cyclohexyl]fluorobenzene.

5. A liquid crystal compound according to claim 1, which is 2-propyl-5-[trans-4-(trans-4-propylcyclohexyl)cyclohexyl]fluorobenzene.

6. A liquid crystal composition comprising at least two components at least one of which is a compound of the formula (a) as set forth in claim 1.

7. A liquid crystal composition according to claim 6, which is a mixture of at least one compound of the formula (a) with at least one nematic liquid crystal compound.

8. A liquid crystal composition according to claim 6, which is a mixture of at least one compound of the formula (a) with a liquid crystal composition consisting of trans-4-propyl-(4-cyanophenyl)cyclohexane, trans-4-pentyl-(4-cycnophenyl)cyclohexane and trans-4-heptyl-(4-cyanophenyl)cyclohexane.

* * * * *